(12) United States Patent
Wen et al.

(10) Patent No.: US 12,161,882 B2
(45) Date of Patent: Dec. 10, 2024

(54) METHOD AND DEVICE FOR IMAT USING ORTHOGONAL DOUBLE LAYER MULTI LEAVES COLLIMATORS

(71) Applicant: SUZHOU LINATECH INTELLIGENT SCIENCE AND TECHNOLOGY CO., LTD., Jiangsu (CN)

(72) Inventors: Hu Er Wen, Jiangsu (CN); Yao Ju, Jiangsu (CN); Jonathan Yi Yao, Jiangsu (CN)

(73) Assignee: SUZHOU LINATECH INTELLIGENT SCIENCE AND TECHNOLOGY CO.,LTD., Jiangsu (CN)

( * ) Notice: Subject to any disclaimer, the term of this patent is extended or adjusted under 35 U.S.C. 154(b) by 337 days.

(21) Appl. No.: 17/618,693

(22) PCT Filed: Nov. 12, 2019

(86) PCT No.: PCT/CN2019/117278
§ 371 (c)(1),
(2) Date: Dec. 13, 2021

(87) PCT Pub. No.: WO2020/248489
PCT Pub. Date: Dec. 17, 2020

(65) Prior Publication Data
US 2022/0241612 A1    Aug. 4, 2022

(30) Foreign Application Priority Data

Jun. 11, 2019 (CN) .......................... 201910500342.2

(51) Int. Cl.
*A61N 5/10* (2006.01)

(52) U.S. Cl.
CPC ......... *A61N 5/1036* (2013.01); *A61N 5/1031* (2013.01); *A61N 5/1047* (2013.01);
(Continued)

(58) Field of Classification Search
CPC ........ A61N 5/10; A61N 5/103; A61N 5/1031; A61N 2005/1034; A61N 5/1036;
(Continued)

(56) References Cited

U.S. PATENT DOCUMENTS 5,818,902 A * 10/1998 Yu ........................ A61N 5/1047
378/65
6,108,400 A * 8/2000 Siochi .................. G01N 23/046
378/65
(Continued)

FOREIGN PATENT DOCUMENTS

| CN | 104318122 A | 1/2015 |
| CN | 105031820 A | 11/2015 |

(Continued)

*Primary Examiner* — Allen C. Ho
(74) *Attorney, Agent, or Firm* — Muncy, Geissler, Olds & Lowe, P.C.

(57) ABSTRACT

The invention provides a method and device for IMAT using orthogonal double layer multi leaves collimators. The method includes: discretizing the rotating arc into multiple equally spaced fields; using the conjugate gradient method to calculate the field intensity matrix; using the double-layer grating static segmentation algorithm to calculate the subfields of each field to obtain the first predetermined number of subfields with the largest contribution to the field of each field; selecting two subfields with similar shapes from the first predetermined number of subfields with the largest contribution, distributing them to the arc of rotation, and performing interpolation to obtain discrete subfields; calculating deposition Matrix; iterative calculation of the shape (Continued)

and weight of subfield; using Monte Carlo dose algorithm to calculate the intensity-modulated dose distribution.

8 Claims, 5 Drawing Sheets

(52) U.S. Cl.
CPC .... *A61N 5/1071* (2013.01); *A61N 2005/1032* (2013.01); *A61N 2005/1034* (2013.01)

(58) Field of Classification Search
CPC .. A61N 5/1042; A61N 5/1045; A61N 5/1047; A61N 5/1048; A61N 5/1071; A61N 2005/1032
USPC .......................................................... 378/65
See application file for complete search history.

(56) References Cited

U.S. PATENT DOCUMENTS

| | | | |
|---|---|---|---|
| 6,314,159 B1 * | 11/2001 | Siochi ................ | A61N 5/1042 378/65 |
| 6,477,229 B1 * | 11/2002 | Grosser ............... | A61N 5/1031 378/65 |
| 6,526,123 B2 * | 2/2003 | Ein-Gal ................ | G21K 1/04 378/65 |
| 6,560,311 B1 * | 5/2003 | Shepard .............. | A61N 5/1031 378/65 |
| 6,661,871 B2 * | 12/2003 | Siochi ................ | A61N 5/1042 378/65 |
| 6,697,452 B2 * | 2/2004 | Xing .................. | A61N 5/1031 378/69 |
| 6,757,355 B1 * | 6/2004 | Siochi ................ | A61N 5/1042 378/65 |
| 6,853,705 B2 * | 2/2005 | Chang ................. | G21K 1/046 378/65 |
| 6,907,105 B2 * | 6/2005 | Otto ................... | G21K 1/046 378/65 |
| 6,907,282 B2 | 6/2005 | Siochi | |
| 7,046,762 B2 * | 5/2006 | Lee .................... | A61N 5/1031 378/65 |
| 7,283,611 B1 * | 10/2007 | Luan ................... | A61N 5/103 378/65 |
| 7,573,978 B2 * | 8/2009 | Kamath ................ | G21K 1/04 378/65 |
| 7,734,010 B2 * | 6/2010 | Otto ................... | A61N 5/1031 378/65 |
| 7,856,082 B2 * | 12/2010 | Flynn .................. | A61N 5/103 378/65 |
| 7,880,154 B2 * | 2/2011 | Otto ................... | A61N 5/1082 378/65 |
| 7,906,770 B2 * | 3/2011 | Otto ................... | A61N 5/1047 378/65 |
| 8,229,071 B2 * | 7/2012 | Stahl .................. | A61N 5/1049 378/65 |
| 8,238,519 B2 * | 8/2012 | Bani-Hashemi ..... | A61N 5/1049 378/65 |
| 8,325,878 B2 * | 12/2012 | McNutt ............... | A61N 5/1031 378/65 |
| 8,401,148 B2 * | 3/2013 | Lu ..................... | A61N 5/1031 378/65 |
| 8,615,068 B2 * | 12/2013 | Gunawardena ...... | A61N 5/1036 378/65 |
| 9,289,627 B2 * | 3/2016 | Otto ................... | G01T 1/29 |
| 9,381,376 B2 * | 7/2016 | Toimela .............. | A61N 5/1064 |
| 9,486,646 B2 * | 11/2016 | Paliwal ............... | A61N 5/1042 |
| 9,750,955 B2 * | 9/2017 | McNutt ............... | A61N 5/1071 |
| 9,919,166 B2 * | 3/2018 | Kontaxis ............. | A61N 5/1031 |
| 9,987,504 B2 * | 6/2018 | Nord ................... | A61N 5/103 |
| 10,617,891 B2 * | 4/2020 | Ramezanzadeh Moghadam ........ A61N 5/1075 |
| 10,744,343 B2 * | 8/2020 | Sjölund ............... | A61N 5/1031 |
| 10,857,386 B2 * | 12/2020 | Sheng ................. | A61N 5/1031 |
| 10,918,888 B2 * | 2/2021 | Ramezanzadeh Moghadam ........ G06N 5/022 |
| 11,167,152 B2 * | 11/2021 | Liu ..................... | A61N 5/103 |
| 11,458,331 B2 * | 10/2022 | Sjölund ............... | A61N 5/1045 |

FOREIGN PATENT DOCUMENTS

| | | |
|---|---|---|
| CN | 105709341 A | 6/2016 |
| CN | 108175953 A | 6/2018 |
| CN | 110215623 A | 9/2019 |

* cited by examiner

Upper blade

| 0 | 0 | 0 | 0 | 0 | 0 | 0 | 0 | 0 |
|---|---|---|---|---|---|---|---|---|
| 0 | 0 | 0 | 1 | 1 | 0 | 0 | 0 | |
| 0 | 0 | 1 | 1 | 1 | 1 | 0 | 0 | |
| 0 | 0 | 0 | 0 | 1 | 1 | 1 | 0 | 0 |
| 0 | 0 | 0 | 1 | 1 | 1 | 0 | 0 | |
| 0 | 0 | 0 | 0 | 1 | 1 | 1 | 0 | 0 |
| 0 | 0 | 0 | 0 | 0 | 0 | 0 | 0 | 0 |

Left blade / Right blade

Lower blade

Fig. 5

Parent1 — Parent2

Child1 — Child2

METHOD AND DEVICE FOR IMAT USING ORTHOGONAL DOUBLE LAYER MULTI LEAVES COLLIMATORS

TECHNICAL FIELD

The present invention relates to the field of medical technology, specifically a method and device for IMAT using orthogonal double layer multi leaves collimators.

BACKGROUND

A basic problem that radiation therapy has been constantly sought to solve as a local treatment of tumors is how to better handle the dose relationship between tumor tissue and surrounding normal tissue, enabling maximum local control and minimal radiation damage to surrounding normal tissue and organs. Clinical experience has shown that the local control of the tumor has some relationship with the radiation damage in the normal tissue. In most cases, the tumor control rate is positively proportional to the normal tissue damage, where increasing the local control rate of the tumors will necessarily cause more damage to the normal tissue. Clinical experience has also demonstrated that radiation damage in normal tissue decreases while maintaining equal levels of tumor control rates through improved irradiation techniques and selection of reasonable time dose factors.

As the most advanced intensity modulation technology, rotary intensity modulation has significant dosimetric advantages compared with fixed field reverse intensity modulation, which can reduce the dose of dangerous organs on the premise of ensuring the uniformity of dose in the target area. At the same time, the frame and grating cooperate to save the treatment time. At present, the rotation intensity modulation technology mainly uses single-layer grating or parallel double-layer grating. However, for conventional single-layer grating, since the blade can only move in one direction, its ability to conform to the thickness direction of the blade is limited; for the parallel double-layer grating, although the blade thickness direction is improved compared with the single-layer grating, it is limited by the blade thickness and can not move or form an irradiation unit at any position. In addition, for complex irradiation intensity, single-layer grating or parallel double-layer grating require multiple subfields to complete the irradiation, and multiple irradiation arcs may be used during rotational intensity modulation. Based on the above reasons, it is difficult to further improve the treatment efficiency under the application of single-layer grating or parallel double-layer grating.

SUMMARY

The purpose of the present invention is to provide a method and device for IMAT using orthogonal double layer multi leaves collimators in order to solve the problem that the rotation intensity modulation is difficult to further improve the treatment efficiency.

In order to achieve the above objectives, the technical solutions adopted by the present invention are as follows:

In the first aspect, the present invention provides a method for IMAT using orthogonal double layer multi leaves collimators, comprising:

discretizing a rotating arc used for radiotherapy into a plurality of equally spaced fields, the plurality of fields having a fixed gantry angle;

calculating the field intensity matrices of the multiple fields by using a conjugate gradient method;

through the double-layer grating static segmentation algorithm, calculating the subfields of each field to obtain the first predetermined number of subfields with the largest contribution of each field;

selecting two subfields with similar shapes from the first predetermined number of subfields with the largest contribution, and distributing them to a rotating arc, and performing interpolation to obtain discrete subfields;

calculating the deposition matrix where the discrete subfields are located;

calculating iteratively the shape and weight of each discrete subfield;

using the Monte Carlo dose algorithm to calculate the intensity-modulated dose distribution.

Optionally, before discretizing the rotating arc used for radiotherapy into a plurality of equally spaced fields, the method further comprises:

determining the number, direction, and range of rotation arcs used for radiotherapy;

setting constraints on the organs to be treated with radiation.

Optionally, through the double-layer grating static segmentation algorithm, calculating the subfields of each field to obtain the first predetermined number of subfields with the largest contribution of each field, it further comprises:

resampling the field intensity matrix at a predetermined sampling interval to obtain the resampled intensity matrix;

the resampled intensity matrix is graded by intensity to obtain equally spaced stepped intensity grades;

the intensity level gradually increases from two, and the subfields of each field are calculated by the double-layer grating static segmentation algorithm until the number of subfields segmented is greater than or equal to the first predetermined number, so as to obtain the first predetermined number of subfields with the greatest contribution of each field.

Optionally, the intensity level gradually increases from two, the subfields of each field are calculated by the double-layer grating static segmentation algorithm until the number of subfields segmented is greater than or equal to the first predetermined number, so as to obtain the first predetermined number of subfields with the greatest contribution of each field, it further comprises:

1) setting the intensity level of two;
2) selecting one-third of the current maximum intensity in the resampled intensity matrix as the segmentation intensity value, and selecting the current segmentation matrix under this segmentation intensity value;
3) calculating the contour of the current segmentation matrix;
4) calculating the actual segmentation matrix with the conformal contour periphery of the upper, lower, left and right blades;
5) calculating the difference between the actual segmentation matrix and the expected segmentation matrix, and if the actual segmentation matrix is greater than the expected segmentation matrix, adjust the blade position so that the actual segmentation matrix is less than or equal to the expected segmentation matrix;
6) subtracting the actual segmentation matrix from the total segmentation matrix of each field to obtain a new total segmentation matrix;

7) calculating the subfield area formed by the actual leaves, if the subfield area is less than the threshold, the subfield leaf position is not retained; if the subfield area is greater than the threshold, the subfield leaf position is retained, and the subfield number is increased by 1;
8) if the new total segmentation matrix is 0, going to step 9), otherwise going to step 2);
9) if the number of subfields is greater than or equal to the first predetermined number, the segmentation is over, otherwise going to step 1), the intensity level increases by 1, and the segmentation is continuing.

Optionally, selecting two subfields with similar shapes from the first predetermined number of subfields with the largest contribution, and distributing them to a rotating arc, and performing interpolation to obtain discrete subfields, it further comprises:
calculating the blade movement distance between the first predetermined number of subfields with the largest contribution respectively;
selecting two subfields with a smaller movement distance, and assigning the two subfields to adjacent angles respectively;
obtaining the shape of the subfield at the frame angle of the field through the interpolation of the subfield position, thereby obtaining discrete subfields with a predetermined spacing, and setting the weight of the discrete subfields to 1.

Optionally, calculating iteratively the shape and weight of each discrete subfield, it further comprises:
a) using genetic algorithm to calculate the shape of each discrete subfield;
b) calculating the weight of each discrete subfield using the conjugate gradient method;
c) executing iteratively steps a) and b) until the number of iterations reaches the specified value or the objective function value is less than the preset threshold.

Optionally, the step a) includes:
A) in the range of the field, performing two-dimensional binary coding on the initial discrete subfields, the value of the occluded part of the blade is 0, the intensity of the beam is 0, the value of the open part of the blade is 1, and the intensity of the beam is 1;
B) the initial population contains a second predetermined number of individuals, each individual represents the third predetermined number of subfields under a plan, each individual corresponds to a fitness value related to the preset objective function, in the case of a positive number, determining the maximum value of the objective function;
C) randomly selecting two parent individuals, and performing crossover operations on the corresponding subfields according to the crossover probability;
D) performing mutation operations on the subfields according to the mutation probability;
E) repeating steps C) and D), when the obtained subfield violates the physical limits of the grating, the dose rate and the gantry angle limits, the current operation will be terminated, and the individual will be reselected for crossover and mutation operations, when the degree value reaches the predetermined threshold or the fitness value of the individual and the group fitness value no longer rise, step E) is ended.

Optionally, using the Monte Carlo dose algorithm to calculate the intensity-modulated dose distribution, it further comprises: outputting the intensity-modulated dose distribution.

In the second aspect, the present invention provides a device for IMAT using orthogonal double layer multi leaves collimators, including:
a rotating arc discretization module, the rotating arc discretization module is used to discretize the rotating arc used for radiotherapy into a plurality of equally spaced fields, the plurality of fields having a fixed gantry angle;
a field intensity matrix calculation module, the field intensity matrix calculation module is used to calculate field intensity matrices of the multiple fields by using a conjugate gradient method;
a subfield calculation module, the subfield calculation module is used to calculate the subfields of each field through the double-layer grating static segmentation algorithm, so as to obtain the first predetermined number of subfields with the largest contribution of each field;
a discrete subfield acquisition module, the discrete subfield acquisition module is used to select two subfields with similar shapes from the first predetermined number of subfields with the largest contribution, and distribute them to a rotating arc, and perform interpolation to obtain discrete subfields;
a deposition matrix calculation module, the deposition matrix calculation module is used to calculate the obtained deposition matrix at the location of the discrete subfields;
an iterative calculation module, the iterative calculation module is used to iteratively calculate the shape and weight of each discrete subfield;
an intensity modulated dose distribution calculation module, the intensity modulated dose distribution calculation module is used to calculate the intensity modulated dose distribution using the Monte Carlo dose algorithm.

Optionally, the device further includes a preprocessing module for:
determining the number, direction and range of the arc of rotation used for radiotherapy;
setting constraints on the organs to be treated with radiation.

Optionally, the subfield calculation module is specifically used for:
resampling the field intensity matrix at a predetermined sampling interval to obtain the resampled intensity matrix;
the resampled intensity matrix is graded by intensity to obtain equally spaced stepped intensity grades;
the intensity level gradually increases from two, and the subfields of each field are calculated by the double-layer grating static segmentation algorithm until the number of subfields segmented is greater than or equal to the first predetermined number, so as to obtain the first predetermined number of subfields with the greatest contribution of each field.

Optionally, the subfield calculation module is also specifically used for:
1) setting the intensity level of two;
2) selecting one-third of the current maximum intensity in the resampled intensity matrix as the segmentation intensity value, and selecting the current segmentation matrix under this segmentation intensity value;
3) calculating the contour of the current segmentation matrix;

4) calculating the actual segmentation matrix with the conformal contour periphery of the upper, lower, left and right blades;
5) calculating the difference between the actual segmentation matrix and the expected segmentation matrix, and if the actual segmentation matrix is greater than the expected segmentation matrix, adjust the blade position so that the actual segmentation matrix is less than or equal to the expected segmentation matrix;
6) subtracting the actual segmentation matrix from the total segmentation matrix of each field to obtain a new total segmentation matrix;
7) calculating the subfield area formed by the actual leaves, if the subfield area is less than the threshold, the subfield leaf position is not retained; if the subfield area is greater than the threshold, the subfield leaf position is retained, and the subfield number is increased by 1;
8) if the new total segmentation matrix is 0, going to step 9), otherwise going to step 2);
9) if the number of subfields is greater than or equal to the first predetermined number, the segmentation is over, otherwise going to step 1), the intensity level increases by 1, and the segmentation is continuing.

Optionally, the discrete subfield acquisition module is specifically used for:
calculating the blade movement distance between the first predetermined number of subfields with the largest contribution respectively;
selecting two subfields with a smaller movement distance, and assigning the two subfields to adjacent angles respectively;
obtaining the shape of the subfield at the frame angle of the field through the interpolation of the subfield position, thereby obtaining discrete subfields with a predetermined spacing, and setting the weight of the discrete subfields to 1.

Optionally, the iterative calculation module is specifically used for:
a) using genetic algorithm to calculate the shape of each discrete subfield;
b) calculating the weight of each discrete subfield using the conjugate gradient method;
c) executing iteratively steps a) and b) until the number of iterations reaches the specified value or the objective function value is less than the preset threshold.

Optionally, the iterative calculation module is also specifically used for:
A) in the range of the field, performing two-dimensional binary coding on the initial discrete subfields, the value of the occluded part of the blade is 0, the intensity of the beam is 0, the value of the open part of the blade is 1, and the intensity of the beam is 1;
B) the initial population contains a second predetermined number of individuals, each individual represents the third predetermined number of subfields under a plan, each individual corresponds to a fitness value related to the preset objective function, in the case of a positive number, determining the maximum value of the objective function;
C) randomly selecting two parent individuals, and performing crossover operations on the corresponding subfields according to the crossover probability;
D) performing mutation operations on the subfields according to the mutation probability;
E) repeating steps C) and D), when the obtained subfield violates the physical limits of the grating, the dose rate and the gantry angle limits, the current operation will be terminated, and the individual will be reselected for crossover and mutation operations, when the degree value reaches the predetermined threshold or the fitness value of the individual and the group fitness value no longer rise, step E) is ended.

Optionally, the device further includes an output module for outputting an intensity-modulated dose distribution.

In a third aspect, the present invention also provides a radiotherapy device, the grating of the device is a double-layer grating with two moving paths orthogonal to each other or arranged at an acute angle, and the device uses the sub-based grating according to the first aspect, the device is controlled by adopting the method for IMAT using orthogonal double layer multi leaves collimators according to the first aspect, or includes the device for IMAT using orthogonal double layer multi leaves collimators according to the second aspect intensity control device.

The Beneficial Effects of the Present Invention Include the method for IMAT using orthogonal double layer multi leaves collimators provided by the present invention includes: discretizing a rotating arc used for radiotherapy into a plurality of equally spaced fields, the plurality of fields having a fixed gantry angle; calculating the field intensity matrices of the multiple fields by using a conjugate gradient method; through the double-layer grating static segmentation algorithm, calculating the subfields of each field to obtain the first predetermined number of subfields with the largest contribution of each field; selecting two subfields with similar shapes from the first predetermined number of subfields with the largest contribution, and distributing them to a rotating arc, and performing interpolation to obtain discrete subfields; calculating the deposition matrix where the discrete subfields are located; calculating iteratively the shape and weight of each discrete subfield; using the Monte Carlo dose algorithm to calculate the intensity-modulated dose distribution. By using the conjugate gradient method to calculate the field strength matrix, and iteratively calculate the shape and weight of each discrete subfield, prevent the optimization calculation process from falling into the local optimal solution, ensure the quality of the plan, and improve the treatment efficiency.

BRIEF DESCRIPTION OF THE DRAWINGS

In order to explain the technical solutions of the embodiments of the present invention more clearly, the accompanying drawings need to be described below. it should be understood that the following drawings show only certain embodiments of the invention and therefore should not be considered as a limitation of scope. For those of ordinary skill in the art, without creative work, other related drawings can be obtained from these drawings.

DETAILED DESCRIPTION OF THE EMBODIMENTS

The technical solutions in the embodiments of the present invention will be clearly and completely described below in conjunction with the accompanying drawings in the embodiments of the present invention. Obviously, the described embodiments are only a part of the embodiments of the present invention, rather than all the embodiments. Based on the embodiments of the present invention, all other embodiments obtained by those of ordinary skill in the art without creative work shall fall within the protection scope of the present invention.

Rotary intensity modulation is the most advanced intensity modulation technology currently developed. Compared with the traditional fixed field reverse intensity modulation, it can reduce the exposure to organs at risk on the premise of ensuring uniform dose uniformity in the target area, and has significant dosimetry advantages. At the same time, the coordinated movement of the gantry and the grating saves treatment time. The initial rotation treatment did not have an optimization process. An arc was divided into several directions, and the shape of the subfield in each direction was determined according to the shape in the Beam's Eye View (BEV). Later, the rotation intensity modulation optimization was developed, and some optimization methods were used to optimize the shape and weight of the subfield in each direction.

At present, the rotation intensity modulation technology mainly uses single-layer grating or parallel double-layer grating. However, there are two problems in the subfield segmentation of single-layer grating and parallel double-layer grating: the degree of conformity in the thickness direction of the blade is not enough; the radiation field requires multiple subfields to be formed, and the irradiation efficiency is low. However, the orthogonal double-layer grating can effectively solve these two problems.

The present invention provides a method and device for IMAT using orthogonal double layer multi leaves collimators based on genetic algorithm and conjugate gradient algorithm. The core of the method is to first discretize the rotating field into a number of fixed fields, optimize the intensity of the fixed fields, and obtain the shape of the segmented subfields through the double-layer grating static segmentation algorithm, and then pass certain screening rules to obtain similar shapes. Then, the genetic algorithm is used to adjust the shape of the double-layer grating blade, and the weight of the conjugate gradient algorithm is adjusted. In the adjustment process, the speed of the grating, the dose rate and the speed of the gantry are comprehensively considered. The method of the present invention will be described in detail below.

Figure 1:
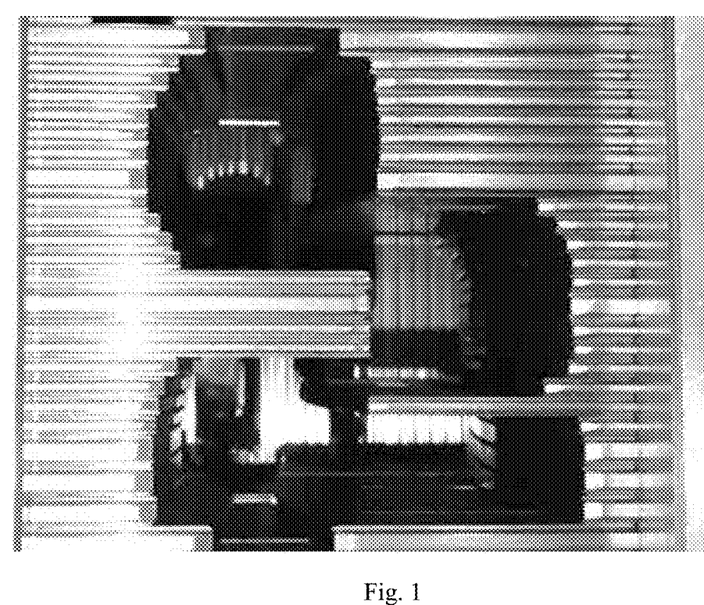
FIG. 1 shows an exemplary picture 1 of an orthogonal double-layer grating for solving subfield segmentation of multiple connected regions according to an embodiment of the present invention.
Figure 2:
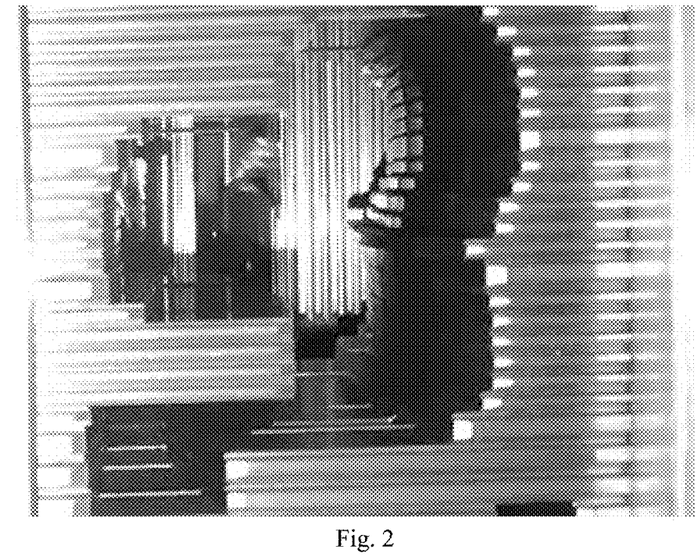
FIG. 2 shows an exemplary picture 2 of an orthogonal double-layer grating for solving subfield segmentation of multiple connected regions according to an embodiment of the present invention.

As shown in FIG. 1 and FIG. 2, the method proposed by the present invention is based on an orthogonal double-layer multi-leaf collimator, which has upper and lower layers of blades, and the direction of movement of the blades of each layer is along the direction perpendicular to the X-ray, and the direction of movement of the two layers of blades is orthogonal. Compared with the traditional single-layer grating and the double-layer parallel grating, the grating has a higher degree of conformity, and the positioning accuracy of less than 1 mm can be achieved in both directions.

The method for IMAT using orthogonal double layer multi leaves collimators provided by the present invention includes:
  discretizing a rotating arc used for radiotherapy into a plurality of equally spaced fields, the plurality of fields having a fixed gantry angle;
  calculating the field intensity matrices of the multiple fields by using a conjugate gradient method;
  through the double-layer grating static segmentation algorithm, calculating the subfields of each field to obtain the first predetermined number of subfields with the largest contribution of each field;
  selecting two subfields with similar shapes from the first predetermined number of subfields with the largest contribution, and distributing them to a rotating arc, and performing interpolation to obtain discrete subfields;
  calculating the deposition matrix where the discrete subfields are located;
  calculating iteratively the shape and weight of each discrete subfield;
  using the Monte Carlo dose algorithm to calculate the intensity-modulated dose distribution.

The present invention uses the conjugate gradient method to calculate the field intensity matrix, and iteratively calculates the shape and weight of each discrete subfield, prevents the optimization calculation process from falling into the local optimal solution, ensures the quality of the plan, and improves the treatment efficiency.

The specific steps of implementing the rotation intensity modulation of the orthogonal double-layer grating will be described in detail below with reference from FIGS. 3 to 7.

Figure 3:
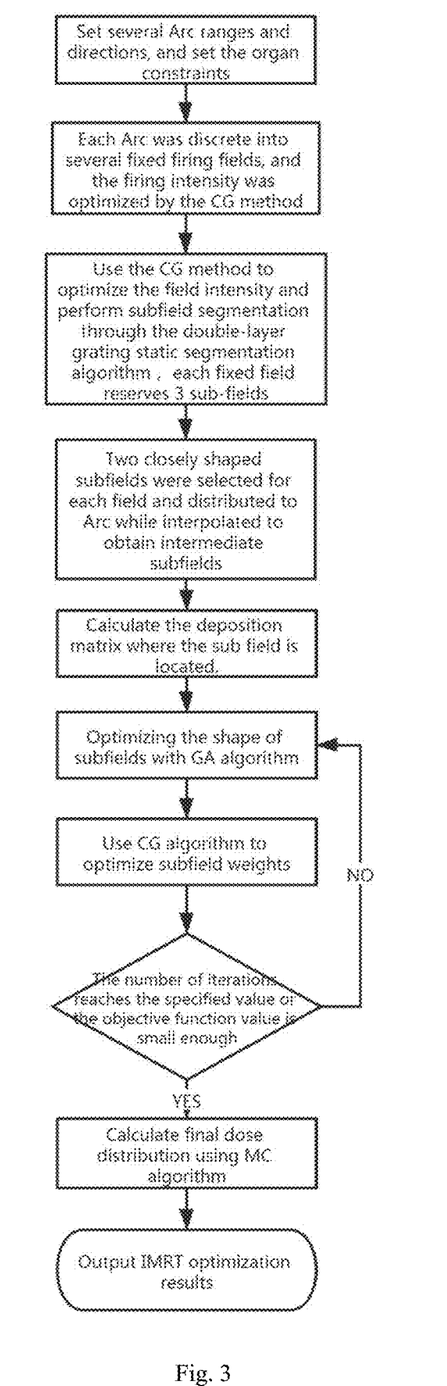
FIG. 3 shows a schematic flowchart of a method for implementing orthogonal double-layer grating rotation intensity modulation based on subfield optimization according to an embodiment of the present invention.

Discretize the rotation arc used for radiotherapy into a plurality of equally spaced fields, the plurality of fields have a fixed gantry angle, and the conjugate gradient method (CG) is used to calculate the field intensity matrix. Specifically, the arc is discretized into several equally spaced fixed gantry angles. The gantry angle is separated by a conjugate gradient method to optimize the intensity distribution of the radiation field. Here is the most commonly used quadratic physical objective function.

The form is as follows:

$$Fobj(x^k) = \alpha \cdot F_{OAR}(x^k) + \beta \cdot F_{PTV}(x^k)$$

$$F_{OAR}(x^k) = \sum_{i=1}^{N_{OAR}} \sum_{j=1}^{NT_i} \delta_j \cdot \omega_j \cdot (d_j(x^k) - p_j)^2$$

$$F_{PTV}(x^k) = \sum_{j=1}^{NT_{PTV}} \delta_j \cdot \omega_j \cdot (d_j(x^k) - p_j)^2$$

$$d_j(x^k) = \sum_{m=1}^{N_{ray}} a_{jm} \cdot x_m^k$$

Among them, $F_{OAR}(x^k)$ is the objective function item related to all OARs, and $F_{PTV}(x^k)$ is the objective function item related to all target regions.

$N_{OAR}$ is the number of OARs, and $NT_i$ is the number of sampling points in the i-th OAR.

$NT_{PTV}$ is the number of sampling points in the target area.

When the point dose in the organ violates the constraint $\delta_j=1$, otherwise $\delta_j=0$.

$\omega_j$ is the weight of the j-th point. $d_j$ is the calculated dose at the j-th point, and $p_j$ is the prescribed dose at the j-th point.

$\alpha$, $\beta$ is the normalization factor that controls the importance of the target area and OAR.

$N_{ray}$ is the total number of ray (also known as pencil beam).

$\alpha_{jm}$ is the m-th beam of unit intensity contributes to the dose of the j-th point.

The whole $\alpha_{jm}$ matrix is called the energy characteristic matrix (or deposition matrix).

$x_m^k$ is the intensity of the m-th beam. In the present invention, the deposition matrix is calculated by the Monte Carlo dose algorithm.

Optionally, discretizing the rotating arc used for radiotherapy into a plurality of equally spaced fields, it further includes:

determining the number, direction, and range of rotation arcs used for radiotherapy;

setting constraints on the organs to be treated with radiation.

Through the double-layer grating static segmentation algorithm (see FIG. 4), the subfields of each field are calculated to obtain the first predetermined number (for example, the first three) subfields that contribute the most to each field. Specifically, the intensity matrix is resampled first: the optimized field intensity distribution matrix $P_{[p \times q]}$ obtained through the above process is resampled to obtain the matrix $D_{[M \times N]}$ and the sampling interval of the matrix in the vertical and horizontal directions is set to 0.25 cm; then the matrix intensity level is divided: Divide the intensity distribution in the previous step into ladder-shaped intensity levels at equal intervals of intensity. The higher the intensity level, the smaller the error between the divided matrix and the original matrix, but at the same time the number of subfields increases. The intensity level gradually increases from 2 until the number of subfields divided is greater than or equal to 3.

Figure 4:
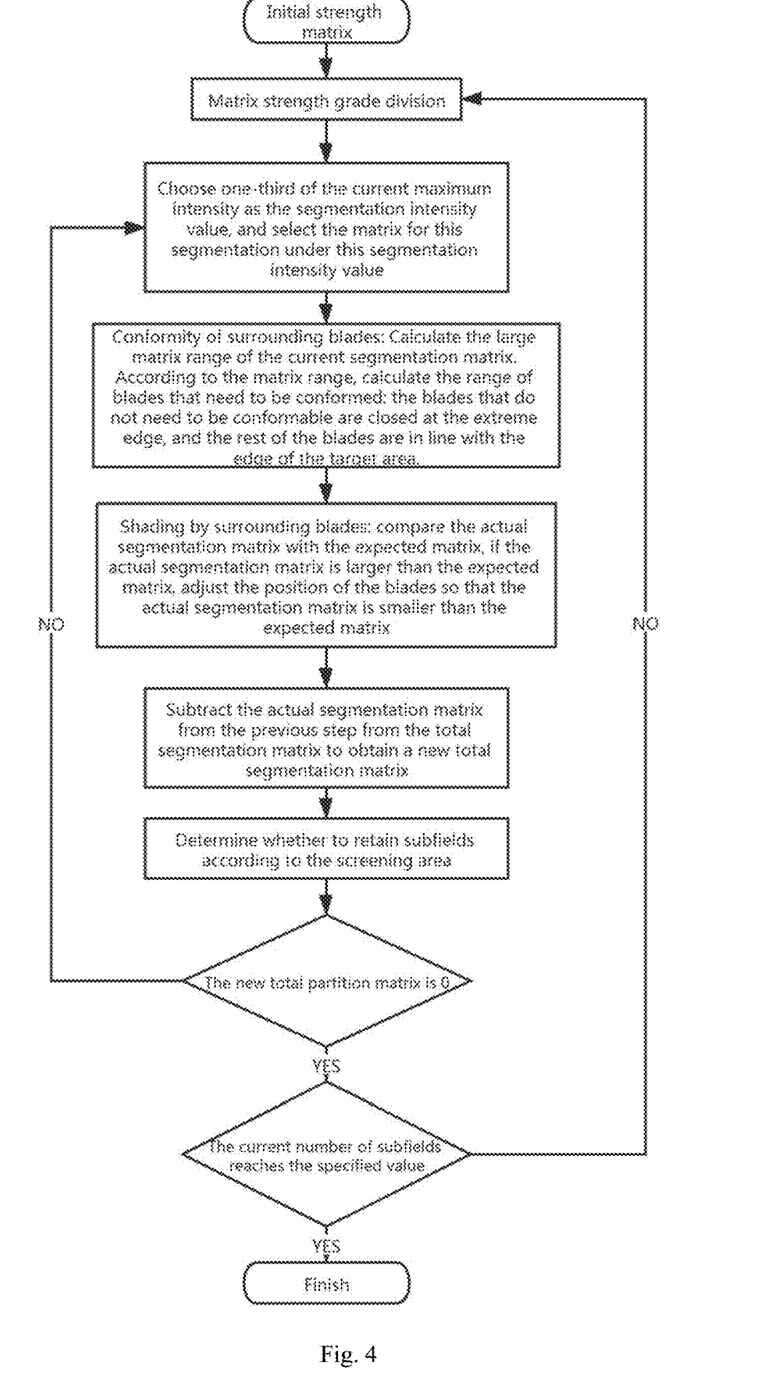
FIG. 4 shows a flowchart of an orthogonal double-layer grating segmentation algorithm provided by an embodiment of the present invention.

The specific segmentation method is as follows:

1) setting the intensity level of two;
2) selecting one-third of the current maximum intensity in the resampled intensity matrix as the segmentation intensity value, and selecting the current segmentation matrix under this segmentation intensity value;
3) calculating the contour of the current segmentation matrix;
4) calculating the actual segmentation matrix with the conformal contour periphery of the upper, lower, left and right blades;
5) calculating the difference between the actual segmentation matrix and the expected segmentation matrix, and if the actual segmentation matrix is greater than the expected segmentation matrix, adjust the blade position so that the actual segmentation matrix is less than or equal to the expected segmentation matrix;
6) subtracting the actual segmentation matrix from the total segmentation matrix of each field to obtain a new total segmentation matrix;
7) calculating the subfield area formed by the actual leaves, if the subfield area is less than the threshold, the subfield leaf position is not retained; if the subfield area is greater than the threshold, the subfield leaf position is retained, and the subfield number is increased by 1;
8) if the new total segmentation matrix is 0, going to step 9), otherwise going to step 2);
9) if the number of subfields is greater than or equal to the first predetermined number, the segmentation is over, otherwise going to step 1), the intensity level increases by 1, and the segmentation is continuing.

Two subfields with similar shapes are selected from the first predetermined number (for example, three) of the subfields with the largest contribution, and distributed to the rotating arc, and interpolation is performed to obtain discrete subfields.

Specifically, for the three subfields with the largest contribution, the movement distances of the blades between the subfields are calculated respectively, and the two subfields with the smaller movement distance are selected, and the two subfields are respectively allocated to adjacent angles. The formula for calculating the movement distance between subfields is as follows:

$$Dis = \sum_{i=0}^{N_{MLC}} \sum_{j=0}^{M_i} \sqrt{(L_{i,j,segm} - L_{i,j,segn})^2 + (R_{i,j,segm} - R_{i,j,segn})^2}$$

Among them, $N_{MLC}$ is the number of grating layers, in this example, the value is 2, which means two layers of grating; $M_i$ is the number of leaves of the i-th grating, and $L_{i,j,segm}$, $L_{i,j,segn}$ is the sub-field segm and sub-field segn respectively in the j-th pair of leaves of the i-th grating on A side, and $R_{i,j,segm}$, $R_{i,j,segn}$ is the sub-field segm and sub-field segn respectively in the j-th pair of leaves of the i-th grating on B side.

Assuming that the gantry angle of the shooting field is $\theta_i$, the gantry angles of the 2 remaining subfields are respectively $\theta_i + \Delta\theta/2$ and $\theta_i - \Delta\theta/2$, and the subfield shape at the same time is obtained by interpolation of the $\theta_i$ subfield position. In this way, we can get a series of discrete subfields with a gantry angle of $\Delta\theta/2$ spacing on Arc, and set the weight of these subfields to 1.

Calculate the obtained deposition matrix at the position of the discrete subfield to update the $\alpha_{jm}$ calculation in the above steps.

Iteratively calculate the shape and weight of each discrete subfield, including: a) using genetic algorithm (GA) to calculate the shape of each discrete subfield; b) using conjugate gradient method (CG) to calculate the weight of each discrete subfield; C) iteratively executing steps a) and b) until the number of iterations reaches the specified value or the objective function value is less than the preset threshold.

Figure 5:
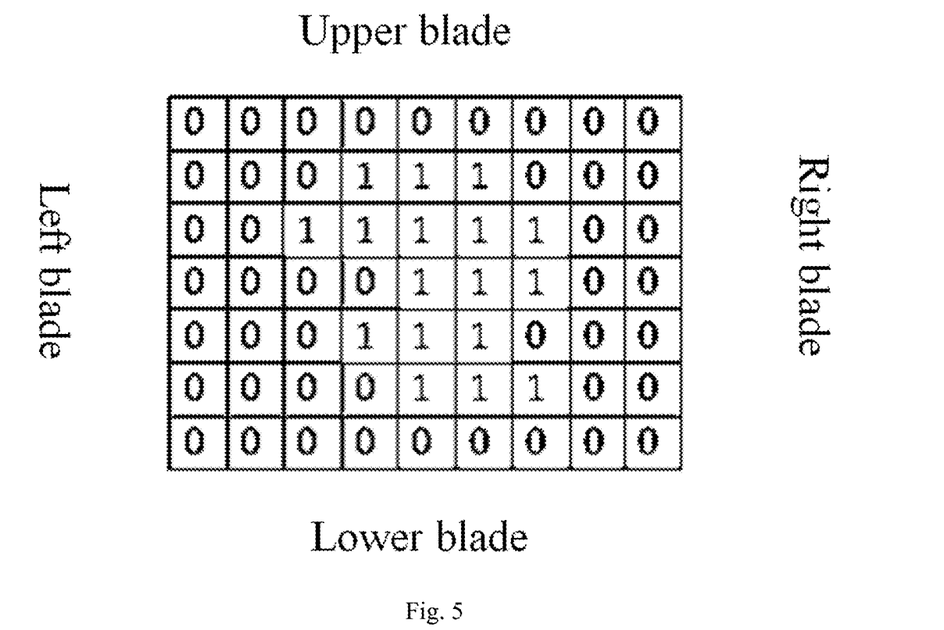
FIG. 5 shows a schematic diagram of two-dimensional binary coding of subfields provided by an embodiment of the present invention.

Among them, step a) specifically includes the following steps:

A) in the range of the field, the initial discrete subfield is two-dimensional binary coded, the value of the occlusion part of the blade is 0, the intensity of the beam is 0, the value of the open part of the blade is 1, and the intensity of the beam is 1 (see FIG. 5);

B) the initial population contains a second predetermined number (for example, N) individuals, each individual represents a third predetermined number (for example, $NS_{total}$) subfields under a plan, and each individual corresponds to a fitness related to the preset objective function Value, under the condition that all fitness values are positive, determine the maximum value of the objective function; the Fitness value calculation formula is as follows:

$$\text{Fitness}(s) = F_{max} - Fobj(s)$$

$$s = (s_1, s_2, \ldots, s_{NS_{total}})$$

Figure 6:
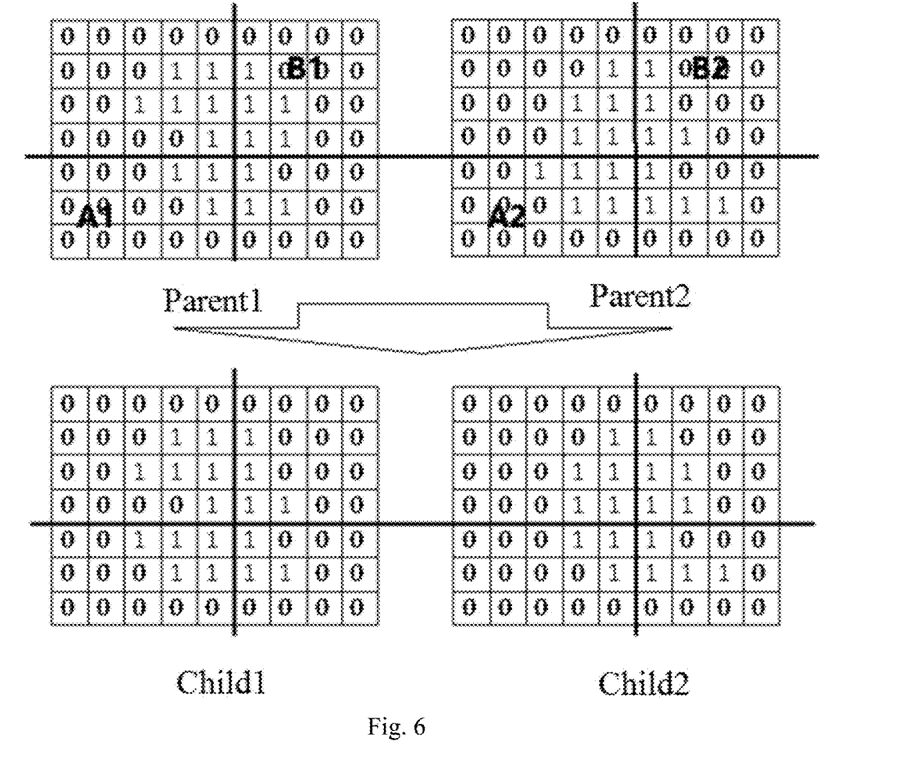
FIG. 6 shows a schematic diagram of genetic algorithm crossover operation provided by an embodiment of the present invention.
Figure 7:
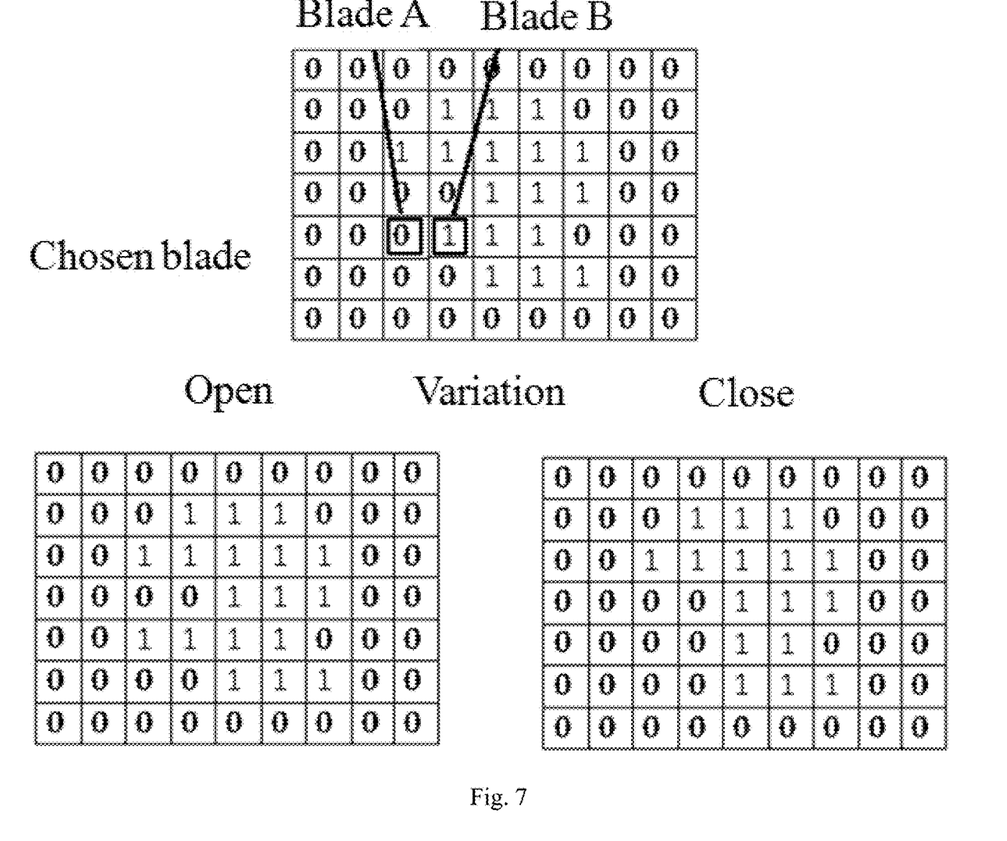
FIG. 7 shows a schematic diagram of genetic algorithm mutation operation provided by an embodiment of the present invention.

Among them, $F_{max}$ is the maximum value of the objective function, and $F_{obj}$ is the objective function, which can be determined according to the maximum value of the objective function corresponding to all individuals in the first-generation population, and it is sufficient to ensure that all fitness values are positive;

C) Crossover: randomly select two parent individuals, and perform crossover operations on the corresponding subfields according to the crossover probability (see FIG. 6);

D) Mutation: perform mutation operation on the subfield according to the mutation probability, that is, randomly select a leaf of the subfield, and then randomly determine whether the leaf is open or closed (see FIG. 7);

E) repeat steps C) and D). When the obtained subfield violates the grating physical limits, dose rate and gantry angle limits, the current operation will be terminated. Reselect individuals for crossover and mutation operations. When the fitness value reaches the predetermined threshold or the fitness value of the optimal individual and the group fitness value no longer rise, step E) is ended, and the loop is out of the loop.

Use the CG algorithm to optimize the weight of the subfield: after each subfield shape optimization, using the CG algorithm in the previous steps to optimize the weight of the subfield. At this time, the grating speed, dose rate, and gantry angle constraints still need to be considered. It should be noted that in this step $\alpha_1$ represents the dose contribution of the m-th subfield of unit weight to the j-th point.

The Monte Carlo dose algorithm (MC) is used to calculate the final intensity-modulated dose distribution to ensure the accuracy of the dose. Optionally, after the Monte Carlo dose algorithm is used to calculate the intensity-modulated dose distribution, the method further includes: outputting an intensity-modulated dose distribution of intensity-modulated radiotherapy (IMRT).

In summary, the method for IMAT using orthogonal double layer multi leaves collimators provided by the embodiment of the present invention can effectively solve the problem of single-layer grating and parallel double-layer grating in realizing reverse rotation intensity modulation. The problem is that the conformality of blade thickness direction is not enough; for complex irradiation intensity, multiple irradiation arcs are required, and the execution efficiency is low. At the same time, the genetic algorithm is used in combination with the conjugate gradient algorithm to prevent falling into the local optimal solution and improve the optimization effect. The application of the present invention can significantly improve the fitness and treatment efficiency, which has extremely important clinical significance.

In addition, the present invention provides a device for IMAT using orthogonal double layer multi leaves collimators, which includes:

a rotating arc discretization module, the rotating arc discretization module is used to discretize the rotating arc used for radiotherapy into a plurality of equally spaced fields, the plurality of fields having a fixed gantry angle;

a field intensity matrix calculation module, the field intensity matrix calculation module is used to calculate field intensity matrices of the multiple fields by using a conjugate gradient method;

a subfield calculation module, the subfield calculation module is used to calculate the subfields of each field through the double-layer grating static segmentation algorithm, so as to obtain the first predetermined number of subfields with the largest contribution of each field;

a discrete subfield acquisition module, the discrete subfield acquisition module is used to select two subfields with similar shapes from the first predetermined number of subfields with the largest contribution, and distribute them to a rotating arc, and perform interpolation to obtain discrete subfields;

a deposition matrix calculation module, the deposition matrix calculation module is used to calculate the obtained deposition matrix at the location of the discrete subfields;

an iterative calculation module, the iterative calculation module is used to iteratively calculate the shape and weight of each discrete subfield;

an intensity modulated dose distribution calculation module, the intensity modulated dose distribution calculation module is used to calculate the intensity modulated dose distribution using the Monte Carlo dose algorithm.

Optionally, the device further includes a preprocessing module, which is used to determine the number, direction and range of the arc of rotation used for radiotherapy; and to set the constraints of the organ to be radiotherapy.

Optionally, the subfield calculation module is specifically configured to: resample the field intensity matrix at a predetermined sampling interval to obtain a resampled intensity matrix; divide the resampled intensity matrix according to intensity levels to obtain equally spaced stepped intensity grades; the intensity level gradually increases from two, and the subfields of each field are calculated by the double-layer grating static segmentation algorithm until the number of subfields divided is greater than or equal to the first predetermined number, so as to obtain the first predetermined number of subfields that contribute the most to each field.

Optionally, the subfield calculation module is further specifically configured to: 1) set the intensity level to two; 2) select one-third of the current maximum intensity in the re-sampling intensity matrix as the segmentation intensity value, and segment it here select the current segmentation matrix under the intensity value; 3) calculate the contour of the current segmentation matrix; 4) calculate the actual segmentation matrix with the contours of the upper, lower, left, and right blades; 5) calculate the difference between the actual segmentation matrix and the expected segmentation matrix, and if the actual segmentation matrix is greater than the expected segmentation matrix, adjust the blade position so that the actual segmentation matrix is less than or equal to the expected segmentation matrix; 6) subtract the actual segmentation matrix from the total segmentation matrix of each field to obtain the new total segmentation matrix; 7) calculate the subfield area formed by the actual leaves. if the subfield area is less than the threshold, the subfield leaf position is not retained; if the subfield area is greater than the threshold, retain the subfield for leaf position, the number of subfields increases by 1; 8) if the new total segmentation matrix is 0, go to step 9), otherwise go to step 2); 9) if the number of subfields is greater than or equal to the first predetermined number, end the segmentation, otherwise go to step 1), increase the intensity level by 1, and continue segmentation. Optionally, the first predetermined number is three, for example.

Optionally, the discrete subfield acquisition module is specifically used to: for calculate the blade movement distance between the first predetermined number of subfields with the largest contribution respectively; select the two subfields with the smaller movement distance, and two subfields are respectively allocated to adjacent angles; obtain the shape of the subfield at the frame angle of the field through the interpolation of the subfield position, thereby obtain discrete subfields with a predetermined spacing, and setting the weight of the discrete subfields to 1.

Optionally, the iterative calculation module is specifically used to: a) use a genetic algorithm to calculate the shape of each discrete subfield; b) use a conjugate gradient method to calculate the weight of each discrete subfield; c) iteratively perform steps a) and b) until the number of iterations reaches the specified value or the objective function value is less than the preset threshold.

Optionally, the iterative calculation module is also specifically used to: A) perform two-dimensional binary coding on the initial discrete subfield within the range of the field, the value of the blade occlusion part is 0, the beam intensity is 0, and the value of the blade opening part is 1, the intensity of the beam is 1; B) the initial population contains a second predetermined number of individuals, each individual represents a third predetermined number of subfields under a plan, and each individual corresponds to a predetermined objective function related the fitness value, under the condition that all fitness values are positive, determine the maximum value of the objective function; C) randomly select two parent individuals, and perform crossover operations on the corresponding child field according to the crossover probability; D) perform mutation operations on the subfields according to the mutation probability; E) repeat steps C) and D), when the obtained subfield violates the physical limits of the grating, dose rate and gantry angle limits, the current operation will be terminated, and the individual will be reselected for crossover, mutation operation, when the fitness value of the individual reaches a predetermined threshold or the fitness value of the individual and the group fitness value no longer rise, end step E).

Optionally, the device further includes an output module for outputting an intensity-modulated dose distribution.

In addition, the present invention also provides a radiotherapy device. The grating of the radiotherapy device is a double-layer grating with two moving paths orthogonal to each other or arranged at an acute angle. The radiotherapy device is controlled by adopting the above-mentioned method for IMAT using orthogonal double layer multi leaves collimators, or includes the above-mentioned device for IMAT using orthogonal double layer multi leaves collimators.

The above-mentioned embodiments are only to illustrate the technical concept and characteristics of the present invention, and their purpose is to allow those of ordinary skill in the art to understand the content of the present invention and implement them, and they cannot limit the scope of protection of the present invention. All equivalent changes or modifications made should be covered by the protection scope of the present invention.

The invention claimed is:
1. A method for IMAT using orthogonal double layer multi leaves collimators, comprising:
    discretizing a rotating arc used for a radiotherapy into a plurality of equally spaced fields, the plurality of equally spaced fields having a fixed gantry angle;
    calculating field intensity matrices of the plurality of equally spaced fields by using a conjugate gradient method;
    through a double-layer grating static segmentation algorithm, calculating subfields of each of the plurality of equally spaced fields to obtain a first predetermined number of the subfields with the largest contribution;
    selecting two subfields with similar shapes from the first predetermined number of the subfields with the largest contribution, and distributing the two subfields to the rotating arc, and performing an interpolation to obtain discrete subfields;
    calculating a deposition matrix where the discrete subfields are located;
    calculating iteratively a shape and a weight of each discrete subfield; and
    using a Monte Carlo dose algorithm to calculate an intensity-modulated dose distribution.

2. The method according to claim 1, wherein before discretizing the rotating arc used for the radiotherapy into the plurality of equally spaced fields, the method further comprises:
    determining a number, a direction, and a range of the rotating arc used for the radiotherapy; and
    setting constraints on organs to be treated with radiation.

3. The method according to claim 1, wherein through the double-layer grating static segmentation algorithm, calculating the subfields of each of the plurality of equally spaced fields to obtain the first predetermined number of the subfields with the largest contribution comprises:
    resampling a field intensity matrix at a predetermined sampling interval to obtain a resampled field intensity matrix;
    the resampled field intensity matrix is graded by an intensity to obtain equally spaced stepped intensity grades;
    the intensity gradually increases from two, and the subfields of each of the plurality of equally spaced fields are calculated by the double-layer grating static segmentation algorithm until a number of subfields segmented is greater than or equal to the first predetermined number of the subfields, so as to obtain the first predetermined number of the subfields with the largest contribution.

4. The method according to claim 3, wherein the intensity gradually increases from two, and the subfields of each of the plurality of equally spaced fields are calculated by the double-layer grating static segmentation algorithm until the number of subfields segmented is greater than or equal to the first predetermined number of the subfields, so as to obtain the first predetermined number of the subfields with the largest contribution comprises:
    1) Setting the intensity of two;
    2) Selecting one-third of the current maximum intensity in the resampled field intensity matrix as a segmentation intensity value, and selecting a current segmentation matrix under the segmentation intensity value;
    3) Calculating a contour of the current segmentation matrix;
    4) Calculating an actual segmentation matrix with a conformal contour periphery of an upper blade, a lower blade, a left blade, and a right blade;
    5) Calculating a difference between the actual segmentation matrix and an expected segmentation matrix, and if the actual segmentation matrix is greater than the expected segmentation matrix, adjusting a blade position so that the actual segmentation matrix is less than or equal to the expected segmentation matrix;

6) Subtracting the actual segmentation matrix from a total segmentation matrix of each of the plurality of equally spaced fields to obtain a new total segmentation matrix;

7) Calculating a subfield area formed by actual leaves, if the subfield area is less than a threshold, a subfield leaf position is not retained; if the subfield area is greater than the threshold, the subfield leaf position is retained, and a subfield number is increased by 1;

8) If the new total segmentation matrix is 0, going to step 9), otherwise going to step 2);

9) if the number of subfields segmented is greater than or equal to the first predetermined number of the subfields, the double-layer grating static segmentation algorithm is over, otherwise going to step 1), the intensity increases by 1, and the double-layer grating static segmentation algorithm is continuing.

5. The method according to claim 4, wherein selecting two subfields with similar shapes from the first predetermined number of the subfields with the largest contribution, and distributing the two subfields to the rotating arc, and performing an interpolation to obtain discrete subfields comprises:

calculating a blade movement distance between the first predetermined number of the subfields with the largest contribution respectively;

selecting two subfields with a smaller movement distance;

assigning the two subfields with the smaller movement distance to adjacent angles respectively; and obtaining a shape of each of the two subfields at a frame angle through an interpolation of a subfield position, thereby obtaining discrete subfields with a predetermined spacing, and setting a weight of the discrete subfields to 1.

6. The method according to claim 1, wherein calculating iteratively the shape and the weight of each discrete subfield comprises:

a) using a generic algorithm to calculate the shape of each discrete subfield;

b) calculating the weight of each discrete subfield using the conjugate gradient method; and c) executing iteratively steps a) and b) until a number of iterations reaches a specified value or an objective function value is less than a preset threshold.

7. The method according to claim 6, wherein the step a) comprises:

A) performing a two-dimensional binary coding on initial discrete subfields, a value of an occluded part of a blade is 0, an intensity of a beam is 0, a value of an open part of the blade is 1, and the intensity of the beam is 1;

B) an initial population contains a second predetermined number of individuals, each individual represents a third predetermined number of subfields under a plan, each individual corresponds to a fitness value related to a preset objective function, in the case of a positive number, determining a maximum value of the present objective function;

C) randomly selecting two parent individuals, and performing crossover operations on the corresponding subfields according to a crossover probability;

D) performing mutation operations on the subfields according to a mutation probability; and E) repeating steps C) and D), when the subfields violate physical limits of a grating, a dose rate and gantry angle limits, a current operation will be terminated, and an individual will be reselected for the crossover operations and the mutation operations, when a degree value reaches a predetermined threshold or the fitness value of the individual and a group fitness value no longer rise, step E) is ended.

8. The method according to claim 1, after using the Monte Carlo dose algorithm to calculate the intensity-modulated dose distribution, further comprising: outputting the intensity-modulated dose distribution.

* * * * *